United States Patent [19]

Widdoes et al.

[11] Patent Number: 4,883,066
[45] Date of Patent: Nov. 28, 1989

[54] HUMAN LIMB MEASURING SYSTEM AND METHOD

[75] Inventors: Harold D. Widdoes, Chadds Ford; Solomon H. Katz, Philadelphia, both of Pa.; Christine E. Cronk, Makanda, Ill.

[73] Assignee: Intersciences Development Associates, Inc., Philadelphia, Pa.

[21] Appl. No.: 154,771

[22] Filed: Feb. 9, 1988

[51] Int. Cl.⁴ .............................................. A61B 5/10
[52] U.S. Cl. ..................................... 128/774; 33/512; 33/515; 33/558
[58] Field of Search ................. 33/511, 512, 515, 558, 33/561, 143 C, 142; 128/774, 782

[56] References Cited

U.S. PATENT DOCUMENTS

| | | | |
|---|---|---|---|
| 3,196,551 | 7/1965 | Provost et al. | 33/515 |
| 3,752,144 | 8/1973 | Weigle | 128/774 |
| 4,539,754 | 9/1985 | Antony et al. | 33/515 |
| 4,567,671 | 2/1986 | Valk | 33/512 |
| 4,603,486 | 8/1986 | Moroney et al. | 33/512 |
| 4,606,128 | 8/1986 | Wynwich et al. | 33/143 C |

Primary Examiner—Lee S. Cohen
Assistant Examiner—John C. Hanley
Attorney, Agent, or Firm—Ratner & Prestia

[57] ABSTRACT

Measuring the length of a human limb by compressing body tissue at the ends of the limb a prescribed amount and then making the length measurement while the body tissue is compressed the prescribed amount.

13 Claims, 3 Drawing Sheets 4,883,066

HUMAN LIMB MEASURING SYSTEM AND METHOD

TECHNICAL FIELD

The present invention relates, in general, to medical diagnostic apparatus and, in particular, to a system and method for measuring the length of the lower leg to detect growth in children.

BACKGROUND ART

Currently, the most widely used method for detecting growth in children is to measure changes in the total height of the child over selected periods of time. Preferably, such measurements should be made as frequently as possible (i.e. at least once every three months), in order to determine whether the treatment prescribed for a child having a particular disorder is enhancing or inhibiting growth or to determine the course of normal growth and development in a child.

A major shortcoming of measuring the total height of the child to detect growth is that serious errors can be introduced in the measurement. For example, variations in spine compression and head posture will contribute to incorrect assessments of actual growth. Consequently, the recommended therapy, based on such measurements, can be inappropriate.

Recognizing this shortcoming of detecting growth by measuring total height, a method and apparatus has been suggested and put into actual use, whereby measurements of the length of the lower leg, are used as a measure of growth. Growth, 1983, 47, 53–66 describes this method and apparatus.

By restricting the measurement of growth to the lower leg, most of the major sources of errors in the measurements of overall height are eliminated entirely. Such measurements have much less relative error than measurement of total body stature which, as indicated above, includes additional variations, for example, in spine compression and head posture. Hence it is possible to reduce the measurement error to such an extent that accurate assessments of growth can be made as frequently as once a month. This can result in a substantial reduction in the cost of various therapies and can assure greater success for the clinical outcome.

The method and apparatus described in the aforementioned article, however, suffers from a major shortcoming which affects the accuracy of the measurements of growth in the lower leg. Typically, the measure of lower leg growth is derived from the average of a number of length measurements made in one measurement session In the method and apparatus described in the aforementioned article, the components which engage the leg and from which the length measurements are made are set to measure directly to the highest attainable height of the knee of the patient. Each such measurement necessarily includes the body tissue above the knee and beneath the heel of the patient. With the top of the knee and the bottom of the foot as the end points of the length measurements, the effects of body tissue above the knee and beneath the heel can introduce errors in the measurements due to variations in the compression of the body tissue from one measurement to the next. The individual conducting the measurements does not know the degree of compression of the body tissue required to duplicate conditions from one measurement to the next. As a result, length measurements subsequent to the first one are biased by looking for the same highest measurement as the first measurement because of a reluctance to rely on the "feel" of the components which engage the endpoints of the leg. To the extent that the individual conducting the length measurements is willing to rely on "feel" to duplicate body tissue compression conditions from one length measurement to the next, accuracy becomes a real concern because of the difficulty in compressing body tissue the same amounts based on the "feel" of the measurer.

DISCLOSURE OF THE INVENTION

Accordingly, a human limb measuring system, constructed in accordance with the present invention, includes means for positioning the limb of a patient in a prescribed position and means for compressing body tissue at the ends of the limb a prescribed amount also included are means responsive to the compressing means for measuring the distance between a selected point on the compressing means and a refrence point while the body tissue is compressed the prescribed amount.

Although the present invention will be described in connection with assessing growth through the measurement of the length of the lower leg, it has at least one other potential application. With suitable modifications to the specific embodiments illustrated in the drawings, the present invention can be adapted for elbow ulnar length measurement.

BRIEF DESCRIPTION OF DRAWINGS

Referring to the drawings.

BEST MODE FOR CARRYING OUT THE INVENTION

Figure 1:
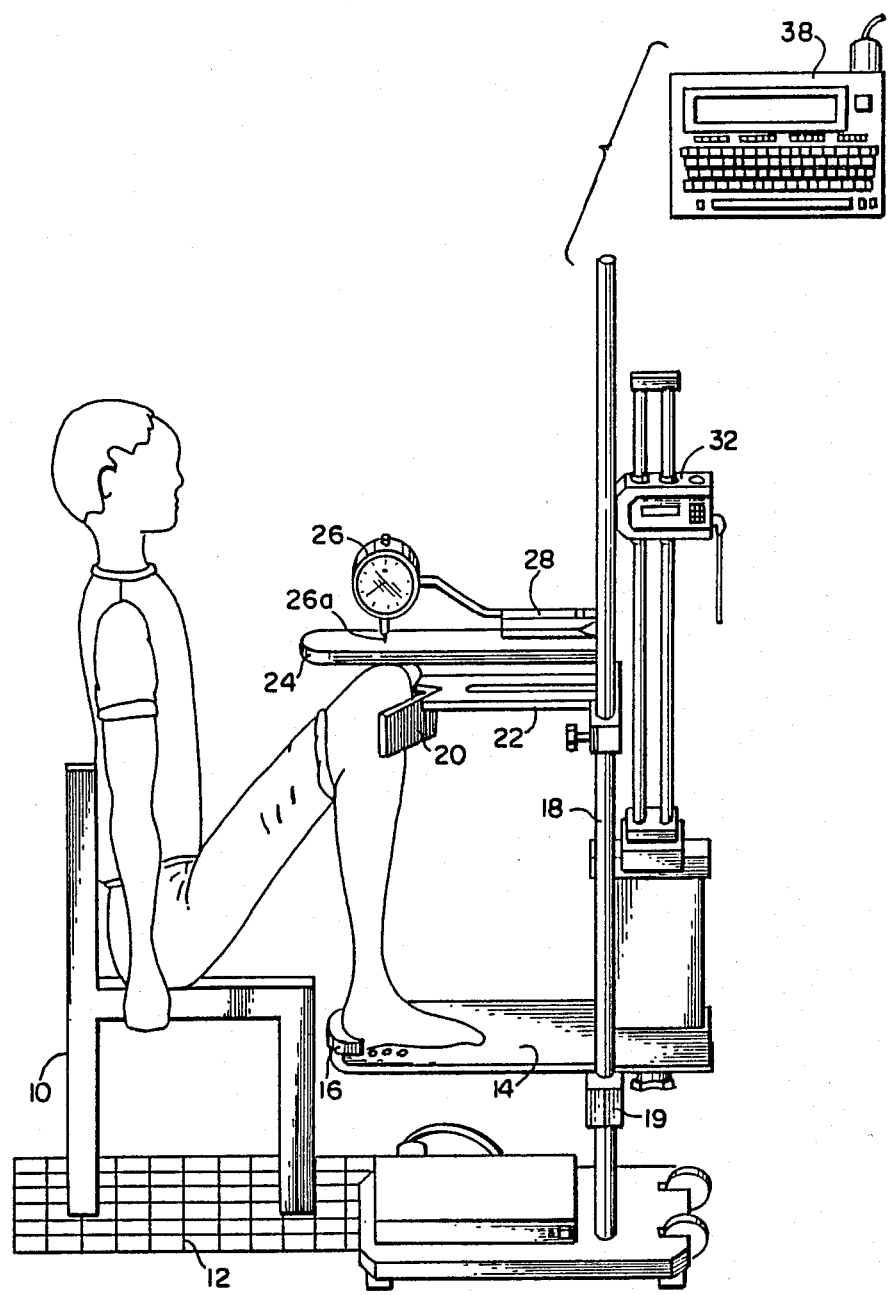
FIG. 1 is a side view of a preferred embodiment of a lower leg measuring system constructed in accordance with the present invention showing a patient in position for measurement of the length of the patient's lower leg.
Figure 2:
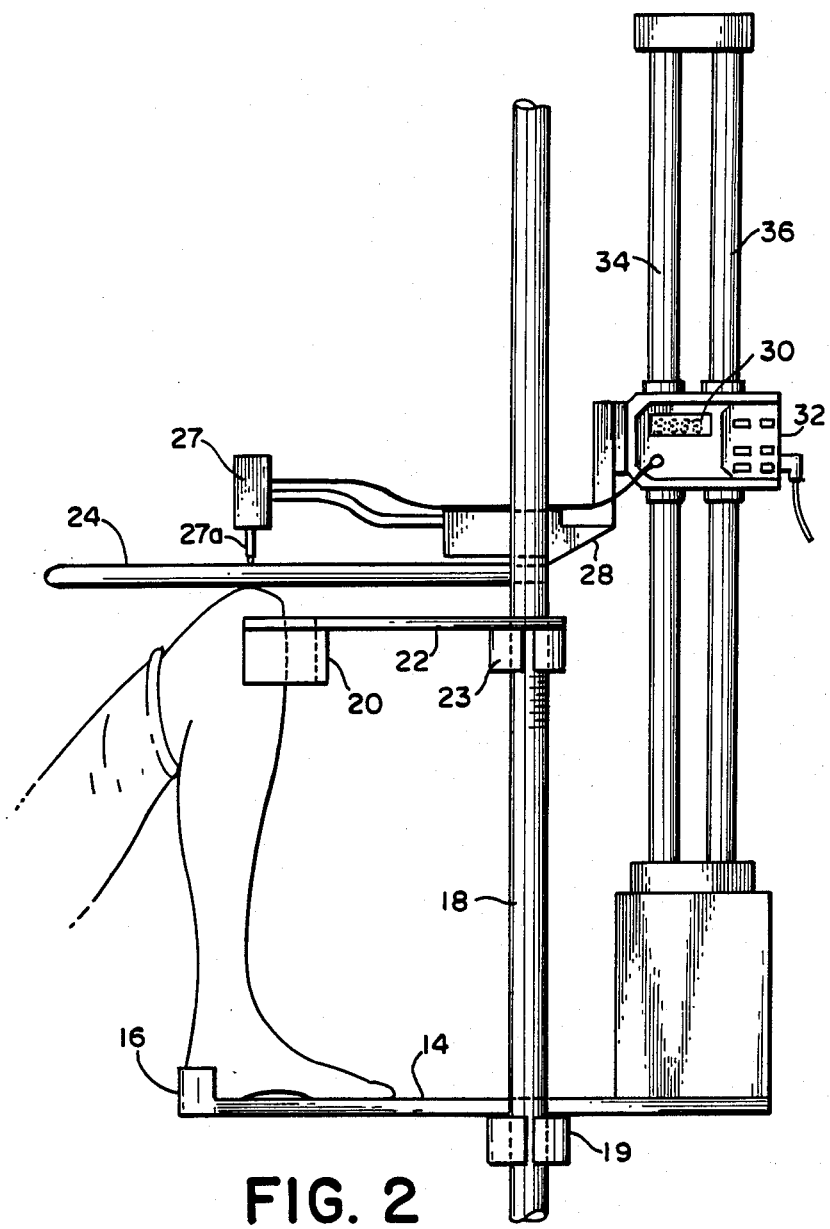
FIG. 2 shows, on an enlarged scale, another version of that portion of the FIG. 1 system which compensates for body tissues which can affect the accuracy of measuring the length of a patient's lower leg.

Referring to FIGS. 1 and 2, a lower leg measuring system, constructed in accordance with the present invention, includes means for positioning the lower leg of a patient in a prescribed position relative to the position of the lower leg for preceding measurements. Preferably, the patient is seated in the same position as he was seated for preceding measurements, the heel of the patient is positioned as it was positioned for preceding measurements, and the knee of the patient is positioned to orient the patient's long bone.

The patient is seated in a chair 10 which is positioned at the same position, from one measurement to the next, either by being fixed in place or by means of a floor grid 12. As will become evident, proper seating of the patient contributes to proper positioning of the leg of the patient.

The heel of the patient is positioned by means of a foot plate 14 and a heel brace 16 mounted on the foot plate. Foot plate 14 either is located at a fixed vertical position or is mounted for vertical movement along a pair of columns 18 (only one of which can be seen in FIGS. 1 and 2) and secured in position at a selected point along the length of the columns by suitable means, such as a pair of collars 19 (only one of which can be seen in FIGS. 1 and 2) fastened to the columns and to which the foot plate is attached. The positioning of foot plate 14 is made adjustable to accommodate different size lower legs and is set to support the foot of the patient in the same vertical position as for preceding measurements.

The position of heel brace 16 on foot plate 14 is set by suitable means, such as by a plurality of lugs carried by the heel brace which fit into correspondingly shaped and positioned holes in the foot plate. Instead of discrete positions for heel brace 16, the heel brace and foot plate 14 can be arranged for continuous movement of the heel brace along the foot plate. The positioning of heel brace 16 is adjustable to accommodate different size feet and is set to position the heel of the patient in the same horizontal position on the foot plate as for preceding measurements. Positioning of the heel establishes one point which will result in a vertical orientation of the long bone of the leg when the leg is set for measurement.

Foot plate 14 and heel brace 16 combine to restrain the heel of the patient against downward movement and sidewise movement. A toe plate can be included to add stability for positioning the foot of the patient. The position of the toe plate would be adjustable to accommodate different size feet.

The knee of the patient is positioned by means of a knee brace 20 and a knee brace plate 22 which are mounted for vertical movement along columns 18. Knee brace 20 can be attached to the knee brace plate 22, so that the horizontal position of the knee brace can be changed Knee brace 20 an knee brace plate 22 can be fixed in position at a selected point along the lengths of columns 18 by suitable means, such as a pair of collars 23 (only one of which can be seen in FIGS. 1 and 2) fastened to the columns and to which the knee brace plate is attached. The positioning of knee brace 20 is adjustable so that with the heel of the patient positioned properly, the knee brace engages the knee of the patient to orient the long bone vertically. The knee of the patient is urged against knee brace 20 by the position in which the patient is seated and the knee brace restrains sidewise movement of the knee.

The lower leg measuring system shown in FIGS. 1 and 2 further includes means for compressing body tissue above the knee of the patient and body tissue below the heel of the patient a prescribed amount. This is accomplished by means of a knee plate 24 and a pressure measuring unit mounted for movement along columns 18. In FIG. 1, the pressure measuring unit is a gauge 26 which provides a visual indication of the compression of the body tissue and, in FIG. 2, the pressure measuring unit is an electro-mechanical sensor 27 which develops an electrical signal having a magnitude representative of the compression of the body tissue.

As knee plate 24 is moved downwardly, the top of the knee is engaged by the knee plate and body tissue above the knee and beneath the heel are compressed. Knee plate 24 is fabricated from a flexible material and deflects as it is moved downward along column 18 due to the resistance against downward movement as the knee plate moves against the knee of the patient The deflection of knee plate 24 is indicated by gauge 26 or the magnitude of the electrical signal developed by sensor 27. The bodies of gauge 26 or sensor 27 are rigidly connected to an angle 28 mounted to move downwardly with knee plate 24 along columns 18. Probe 26a of gauge 26 or probe 27a of sensor 27 measure the deflection of knee plate 24. The downward movement of knee plate 24 is stopped when gauge 26 produces a prescribed reading or sensor 27 develops an electrical signal having a prescribed magnitude as indicated by a display 30 of a computer interface 32 to which sensor 27 is connected.

The lower leg measuring system shown in FIGS. 1 and 2 also includes means responsive to the compressing means for measuring the distance between a selected point on the compressing means and a reference point while the body tissue above the knee of the patient and beneath the heel of the patient is compressed the prescribed amount. Such means can take a variety of forms. For example, as illustrated in FIG. 2, a scale may be arranged on one of the columns 18 which can be read directly by noting the position of knee plate 24 along the scale. In an alternative form, a scale may be arranged on one of a pair of columns 34 or 36, so that a position sensor, mounted for movement with computer interface 32, along columns 34 and 36, senses its location along the scale to produce an indication of the location of the position sensor. In this arrangement, computer interface 32 is attached to angle 28, as shown in FIG. 2, so that the computer interface moves vertically with knee plate 24.

For the embodiment of the invention illustrated in FIGS. 1 and 2, the verticial position of foot plate 14 serves as a reference point for measuring the length of the lower leg of the patient while the body tissue above the knee and beneath the heel is compressed. The distance between the bottom of knee plate 24 and the top of foot plate 14 represents the desired measurement.

A computer 38 serves to store indications of the length of the lower leg of the patient and to process signals representative of such indications to develop various bits of information, such as changes in the length of the lower leg from one measurement session to the next. In addition, computer 38 serves to store information representative of the positions of the different components of the system, so that when conducting subsequent measurements of the lower leg, the components can be set to position the lower leg properly.

Figure 3:
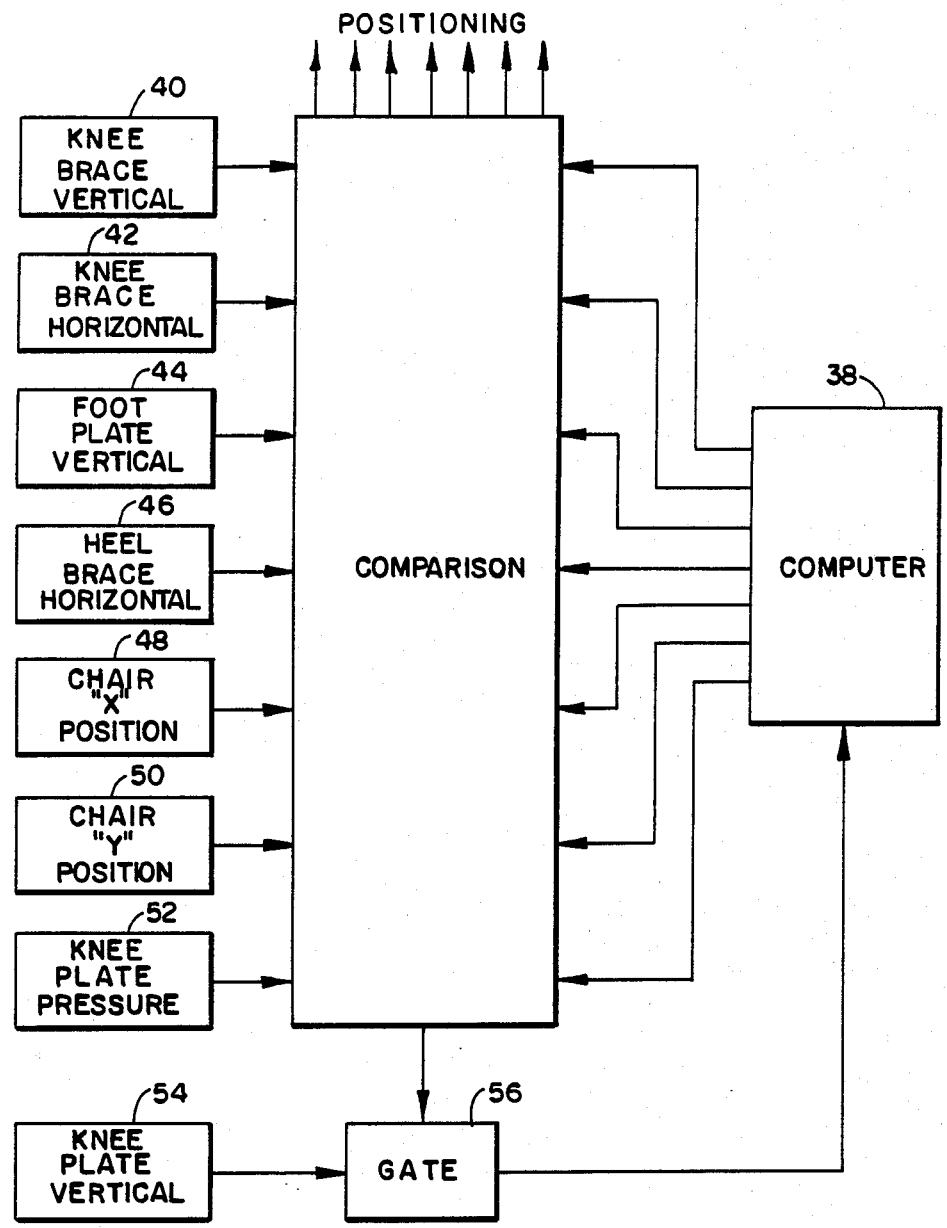
FIG. 3 is a block diagram which illustrates the operational sequence of FIG. 1 system.

FIG. 3 is a block diagram which illustrates the operational sequence of the FIGS. 1 and 2 system. When the lower leg of a patient is to be measured, computer 38 is accessed to provide previously stored information regarding the positions of chair 10, foot plate 14, heel brace 16, and knee brace 20. (This assumes that chair 10 and footplate 14 are movable). In addition, computer 38 provides information as to the degree to which body tissue above the knee and beneath the heel is to be compressed. The various components of the system are set either manually or automatically at positions corresponding to the stored information. In this way, the lower leg of the patient will be positioned as it was for prior measurements. With the lower leg of the patient positioned properly, the length measurement is taken and stored in computer 38.

For automatic operation, blocks 40, 42, 44, 46, 48, 50 and 52 in FIG. 3 represent sensors which sense the indicated parameters. (This again assumes that chair 10 and footplate 14 are movable). The signals from these sensors are compared with the corresponding information retrieved from computer 38. The notation "POSITIONING" represents controls for operating servo motors or the like which drive the various components which position the lower leg for measurements. These components are moved until the sensed positions of these components correspond to the information supplied by computer 38. At that time, the lower leg measurement, represented by block 54, is passed to computer 38 through a gate 56 which is opened when the sensed positions of the components correspond to the desired positions of the components. In this case, no visual indication of body tissue compression is required. Information about the vertical position of the knee plate is generated continuously and when the sensed body tissue compression corresponds to the stored body tissue compression gate 56 is triggered to pass the information about the vertical position of the knee plate at that moment.

The foregoing has set forth exemplary and preferred embodiments of the present invention It will be understood, however, that various alternatives will occur to those of ordinary skill in the art without departure from the spirit and scope of the present invention.

We claim:

1. A human limb measuring system comprising:
   means for positioning and restraining the limb of a patient in a prescribed repeatable position;
   means for compressing body tissue at the ends of said limb a prescribed amount;
   and means responsive to said compressing means for measuring the distance between a selected point on said compressing means and a reference point while said body tissue is compressed said prescribed amount.

2. A human limb length measuring system according to claim 1 wherein said compressing means include:
   (a) a flexible member;
   (b) means for moving said flexible member against a selected part of said limb to compress said body tissue and deflect said flexible member as said body tissue is compressed, and
   (c) means for measuring the deflection of said flexible member to develop an indication of the amount of compression of said body tissue and stop movement of said flexible member when said body tissue is compressed said prescribed amount.

3. A human limb length measuring system according to claim 3 wherein said positioning and restraining means include:
   (a) first means for restraining one end of said limb against movement along the axis of the long bone of said limb and transverse to said axis, and
   (b) second means for restraining the other end of said limb against movement transverse to said axis.

4. A human limb length measuring system according to claim 4 and adapted to measure a lower leg wherein:
   (a) said first means of said positioning and restraining means include a foot plate means for supporting the foot of the patient and a heel brace means for positioning the heel of the patient in a repeatable horizontal position on said foot plate means, and
   (b) said second means of said positioning and restraining means include a knee brace means mounted for vertical movement to engage the knee of the patient for positioning the long bone of the patient in a repeatable orientation.

5. A human limb length measuring system according to claim 5 wherein said flexible member is a knee plate and said means for moving said flexible member include means for mounting said knee plate for vertical movement against the top of the knee of the patient for compressing body tissue above the knee and beneath the heel.

6. A human limb measuring system comprising:
   means for positioning and restraining the limb of a patient in a prescribed repeatable position;
   means for compressing body tissue at the ends of said limb a prescribed amount;
   means responsive to said compressing means for measuring the distance between a selected point on said compressing means and a reference point while said body tissue is compressed said prescribed amount;
   and means for storing information representative of the position of said limb while said limb is in said prescribed position and for retrieving said information to reposition said limb in said prescribed position in the future.

7. A lower leg measuring system comprising:
   means for positioning the lower leg of a patient in the same position as for preceding measurements which have been made on the patient, said positioning means including:
   (a) a chair fixed in place for the patient to sit on,
   (b) a foot plate means for supporting the foot of the patient in the same vertical position as for preceding measurements,
   (c) means on said foot plate means for positioning the heel of the patient in the same horizontal position on said foot plate means as for preceding measurements;
   (d) a knee brace means for engaging the knee of the patient for orienting the long bone of the patient as for preceding measurements, and
   (e) means for mounting said knee brace means for vertical movement of said knee brace means;
   a flexible knee plate means for compressing body tissue above the knee and beneath the heel;
   means for mounting said flexible knee plate means for vertical movement against the top of the knee of the patient;
   pressure sensing means responsive to deflection of said knee plate means as said knee plate means moves against the knee of the patient for developing an indication of the compression of the body tissue above the knee of the patient and beneath the heel of the patient to set the vertical position of said knee plate means when the body tissue above the knee and beneath the heel has been compressed the same amount as for preceding measurements;
   means for measuring the vertical distance between said foot plate means and said vertical position of said knee plate means to develop an indication of the length of the lower leg of the patient;
   and means for storing said indication of the length of the lower leg of the patient and for comparing said indication of the length of the lower leg with similar indications developed for preceding measurements.

8. A lower leg measuring system comprising: means for positioning the lower leg of a patient in the same position as for preceding measurements which have been made on the patient, said positioning means including:
   a chair for the patient to sit on,
   a floor grid means for positioning said chair in the same position as for preceding measurements;

(c) a foot plate means for supporting the foot of the patient in the same vertical position as for preceding measurements, (d) means on said foot plate means for positioning the heel of the patient in the same horizontal position on said foot plate means as for preceding measurements, (e) a knee brace means for engaging the knee of the patient for orientating the long bone of the patient as for preceding measurements, and (f) means for mounting said knee brace means for vertical movement of said knee brace means;

a flexible knee plate means for compressing body tissue above the knee and beneath the heel;

means for mounting said flexible knee plate means for vertical movement against the top of the knee of the patient;

pressure sensing means responsive to deflection of said knee plate means as said knee plate means moves against the knee of the patient for developing an indication of the compression of the body tissue above the knee of the patient and beneath the heel of the patient to set the vertical position of said knee plate means when the body tissue above the knee and beneath the heel has been compressed the same amount as for preceding measurements;

means for measuring the vertical distance between said foot plate means and said vertical position of said knee plate means to develop an indication of the length of the lower leg of the patient;

and means for storing said indication of the length of the lower leg of the patient and for comparing said indication of the length of the lower leg with similar indications developed for preceding measurements.

9. A lower leg measuring system according to claim 7 further including means for mounting said knee brace means for horizontal movement of said knee brace means.

10. A method for measuring a human limb comprising the steps of:

positioning the limb of a patient in a prescribed position;

compressing body tissue of the limb at the ends of the limb a prescribed amount;

developing an indication of the compression of said body tissue;

and measuring the distance between the ends of the limb when said indication of compression of said body tissue corresponds to said prescribed amount.

11. A method for measuring a human limb according to claim 10 further including the step of storing information representative of the position of the limb while the limb is in said prescribed position.

12. A method for measuring a human limb according to claim 11 wherein said steps are repeated with said limb repositioned in said prescribed position according to the stored information.

13. A method for measuring a human limb comprising the steps of:

positioning the limb of a patient in a prescribed position;

compressing body tissue of the limb at the ends of the limb in a prescribed amount;

developing an indication of the compression of said body tissue;

measuring the distance between the ends of the limb when said indication of compression of said body tissue corresponds to said prescribed amount;

storing information representative of the position of the limb while the limb is in said prescribed position;

retrieving said information representative of the position of the limb;

comparing the positioning of the limb against said information representative of the position of the limb;

and positioning the limb in said prescribed position according to said information representative of the position of the limb.

* * * * *